United States Patent [19]
Jacobs

[11] Patent Number: 5,968,073
[45] Date of Patent: Oct. 19, 1999

[54] METHODS AND APPARATUS FOR APPLYING PRESSURE

[76] Inventor: Laura F. Jacobs, 8 Haegoz St., Kochav Yair, Israel, 44864

[21] Appl. No.: 08/971,864

[22] Filed: Nov. 17, 1997

[51] Int. Cl.⁶ .................................................. A61B 17/00
[52] U.S. Cl. ........................................... 606/202; 606/203
[58] Field of Search ................................. 606/201, 202, 606/203, 204; 128/24 R, 33, 64, 70, 680, 683, 668

[56] References Cited

U.S. PATENT DOCUMENTS

| | | |
|---|---|---|
| 4,370,975 | 2/1983 | Wright . |
| 4,773,397 | 9/1988 | Wright et al. . |
| 4,865,020 | 9/1989 | Bullard ...................................... 128/64 |
| 4,889,132 | 12/1989 | Hutcheson et al. ...................... 128/680 |
| 4,922,893 | 5/1990 | Wright et al. . |
| 5,437,610 | 8/1995 | Cariapa et al. . |
| 5,575,762 | 11/1996 | Peeler et al. . |
| 5,591,200 | 1/1997 | Cone et al. . |

*Primary Examiner*—Michael Buiz
*Assistant Examiner*—Vy Q. Bui
*Attorney, Agent, or Firm*—Ostrolenk, Faber, Gerb & Soffen, LLP

[57] ABSTRACT

Apparatus for applying pressure to a portion of a body, including a pressure cuff surroundingly engageable with the portion of the body, the cuff including a plurality of individually inflatable cells, including a most distal cell and a most proximal cell, and a pressure controller that inflates at least one of the cells to a non-constant pressure during a given time period. Preferably the pressure fluctuates between predetermined maximum and minimum levels during each time interval of cell inflation. The easing of pressure allows the engorged tissue to which the cell applies pressure to immediately refill between pressure rises to the maximum pressure. The cell thus dynamically decongests the engorged tissue to which the cell applies pressure.

10 Claims, 5 Drawing Sheets

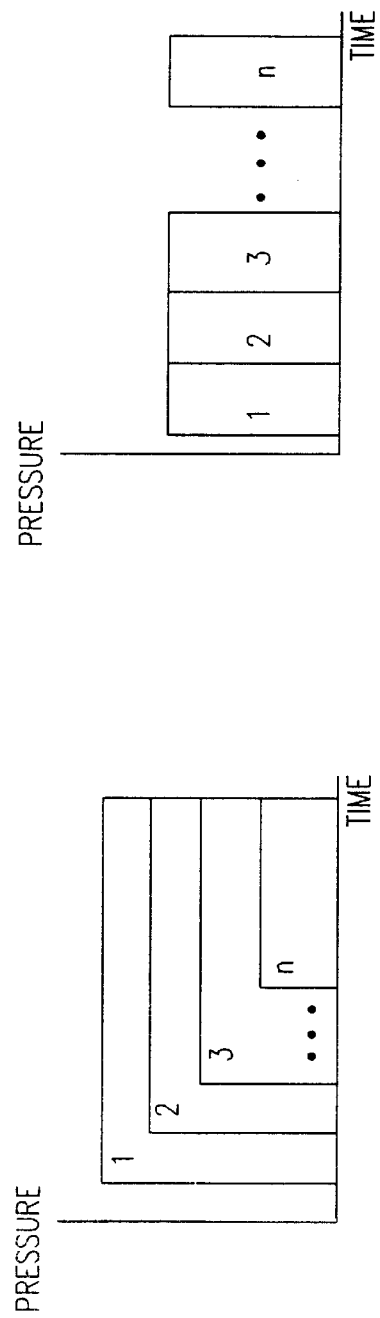

METHODS AND APPARATUS FOR APPLYING PRESSURE

FIELD OF THE INVENTION

The present invention relates generally to methods and apparatus for applying pressure to a portion of a body and particularly to methods and apparatus for application of a peristaltic pulse wave pressure for treating edematous or circulatory/lymphatic conditions.

BACKGROUND OF THE INVENTION

Edematous conditions, i.e., excessive accumulation of fluid in tissues, are painful conditions that can arise from a variety of causes. For example, preoperative, operative and postoperative immobilization of limbs can cause blood stasis and venous thromboembolism, a serious edematous condition. The swelling of limbs in edematous conditions can be unsightly and ultimately life threatening.

It is well known to treat edema with pressure devices that squeeze the limb, typically by means of an inflatable pressure cuff wrapped around the limb. The pressure device moves excess fluid from engorged tissues from distal portions of the limb to proximal portions, eventually to the trunk of the body where the fluids are absorbed in the circulatory system and excreted from the body. These pressure devices thus perform external, non-invasive compression therapy.

The prior art uses basically four different techniques to apply the pressure, known as wave forms. The first type of wave form is non-sequential and non-gradient and is shown in FIG. 1A. A pressure cuff is wrapped around the limb and inflated to a certain pressure for squeezing the limb and forcing the excess fluid to flow proximally (at least supposedly) to the trunk of the body. This wave form is of course quite simple and basic, but suffers from several drawbacks. First of all, there is quite a bit of discomfort at high pressures. Secondly, the pressure cuff collapses all veins and lymphatics throughout the limb, which can have deleterious side effects. Thirdly, as the length of the pressure cuff increases, the more distal regions of the limb are not effectively decongested of fluid. Fourthly, the somewhat uniform application of pressure does not effectively direct the flow in the proximal direction.

The other three wave forms recognize that in edematous conditions the fluid flow is poorly directed in the proximal direction, and each wave form attempts to solve the problem in a different manner. All three remaining wave forms employ a pressure cuff constructed with a plurality of inflatable pouches, called cells, located along the length of the limb, there being a most distal cell and a most proximal cell. What distinguishes the three other wave forms of the prior art from each other is the manner in which the cells are inflated.

The second type of wave form is sequential and non-gradient and is shown in FIG. 1B. The most distal cell is inflated, followed sequentially by the second most distal cell and so on up to the most proximal cell. The most distal cell is maintained inflated all the time up to and including inflation of the most proximal cell in order to reduce backflow, i.e., distally directed flow. However, this method still has the disadvantage of discomfort at high pressures. The most distal cell is particularly painful because it is inflated during the entire therapy. In contrast, the most proximal cell is not inflated long enough. Moreover, as soon as one cell inflates, it acts as a barrier to the more distal cells and hinders the fluid from draining proximally.

The third type of wave form is sequential and gradient and is shown in FIG. 1C. The most distal cell is inflated to a relatively high pressure, followed sequentially by inflating the second most distal cell to a slightly lower pressure and so on down to the most proximal cell. The distal cells remain inflated throughout the therapy cycle to reduce backflow. However, this wave form still has the disadvantage of the most distal cell being inflated too long and the most proximal cell not being inflated long enough. Moreover, in order to ensure creating a pressure gradient from the distal end to the proximal end, the most distal cell must be inflated to a very high pressure and the most proximal cell is usually insufficiently pressurized, thus impairing the efficiency of the method.

The sequential and gradient wave form is used in several US Patents. U.S. Pat. No. 4,370,975 to Wright describes apparatus for promoting flow of a body fluid in a human limb. Timing valves are used to inflate the cells in accordance with a timing control sequence.

U.S. Pat. No. 5,575,762 to Peeler et al. describes a gradient sequential compression system and method for reducing the occurrence of deep vein thrombosis. The system has a controller that includes a plurality of feeder valves pneumatically connected to each of the cells and a microprocessor-based control unit for opening only one of the feeder valves at a time during an inflation cycle, so that each of the cells can be independently inflated to predetermined pressure levels. The controller regulates the pressures in each of the cells by repeatedly measuring the pressures and making any necessary adjustments.

U.S. Pat. No. 5,591,200 to Cone et al. describes apparatus for treating edema by applying pressure to a patient's limb. The apparatus includes electrically-operated valves for controlling inflation of the cells. A computer individually controls each valve to variably pressurize the cell in a variable sequence. The computer also has a determiner for determining the girth of the limb being treated.

In all of the three abovementioned patents, although pressure measuring means are provided, the pressure remains substantially constant for each time interval. The inflation of each cell is controlled only as a function of time, not pressure. Wright uses timing valves. In Cone et al., it is essential to use a timer for measuring the time period for filling each cell and for generating a timing signal in response to the cell filling. In Peeler et al., as mentioned above, the pressures in each of the cells are repeatedly measured. However, the pressure measurement is only for purposes of adjusting and maintaining the pressure at a substantially constant level; not for changing the pressure in any given time cycle or increment.

The fourth type of wave form is peristaltic and is shown in FIG. 1D. The most distal cell is inflated to a tourniquet pressure, followed sequentially by inflating the second most distal cell to the tourniquet pressure. The most distal cell is deflated once the second most distal cell has reached the tourniquet pressure. The process continues in this fashion for each neighboring pair of cells until the most proximal cell is reached. Thus the cells are peristaltically filled which helps ensure proximally directed flow and reduce backflow. Again the inflation of each cell is controlled as a function of time, not pressure. A disadvantage of this method is that since the cells are inflated to tourniquet pressure, they cannot remain inflated for very long. The relatively short compression time reduces the efficiency of the method.

SUMMARY OF THE INVENTION

The present invention seeks to provide novel apparatus for pressure therapy that uses a novel wave form, herein called the peristaltic pulse wave form. The peristaltic pulse wave form is similar to the prior art peristaltic wave form in that neighboring cells are sequentially filled to tourniquet pressure to achieve proximal flow and reduce backflow. However, the similarity ends there. Unlike the regular peristaltic wave form, the present invention does not inflate the cell to a constant pressure. Instead, the pressure fluctuates between predetermined maximum and minimum levels during each time interval of cell inflation. The easing of pressure allows the engorged tissue to which the cell applies pressure to immediately refill between pressure rises to the maximum pressure. The cell thus dynamically decongests the engorged tissue to which the cell applies pressure, even achieving decongestion of deep layers of tissue. Pressure is not maintained constant, but is repeatedly attained in a pulsed manner. Therefore, the veins, lymphatics and other tissue channels are not collapsed for long periods of time and discomfort is reduced, while at the same time the pressure pulses are sufficient to efficiently decongest the limb or other body portion. Following the pulsed decongestion a tourniquet pressure is employed to prevent backflow. None of the prior art methods or apparatus have dynamic decongestion, immediate refill, and cell inflation changing as a function of pressure.

There is thus provided in accordance with a preferred embodiment of the present invention apparatus for applying pressure to a portion of a body, including a pressure cuff surroundingly engageable with the portion of the body, the cuff including a plurality of individually inflatable cells, including a most distal cell and a most proximal cell, and a pressure controller that inflates at least one of the cells to a non-constant pressure during a given time period.

In accordance with a preferred embodiment of the present invention the pressure controller inflates at least one of the cells to a pressure that fluctuates between a maximum value and a minimum value during the given time period.

Further in accordance with a preferred embodiment of the present invention the pressure controller inflates at least one of the cells with pulses of pressure, the pressure fluctuating between a maximum value and a minimum value during the given time period.

Still further in accordance with a preferred embodiment of the present invention, for each neighboring pair of cells including a more distal cell and a more proximal cell, the pressure controller inflates the more distal cell to a tourniquet pressure at the end of the given time period, then inflates the more proximal cell to the tourniquet pressure, the more distal cell being deflated once the more proximal cell has reached the tourniquet pressure.

Additionally in accordance with a preferred embodiment of the present invention the pressure controller includes a source of pressure and a plurality of valves, each valve being dedicated to a particular one of the cells, and each valve being in fluid communication with both the source of pressure and the particular cell.

Preferably each cell includes a pressure sensor for sensing a pressure of inflation and deflation of the cell. The pressure controller may inflate the cells in accordance with a programmable inflation scheme.

In accordance with a preferred embodiment of the present invention there is provided a volumetric sensor that measures a volumetric change in the inflatable cells.

There is also provided in accordance with a preferred embodiment of the present invention apparatus for measuring a portion of a body, including an inflatable cell inflatable about a portion of a body, and a volumetric sensor that measures a volumetric change in the inflatable cell.

There is also provided in accordance with a preferred embodiment of the present invention a method for applying pressure to a portion of a body, including attaching a pressure cuff around the portion of the body, the cuff including a plurality of individually inflatable cells, including a most distal cell and a most proximal cell, and inflating at least one of the cells to a non-constant pressure during a given time period.

In accordance with a preferred embodiment of the present invention the method includes inflating at least one of the cells to a pressure that fluctuates between a maximum value and a minimum value during the given time period.

Further in accordance with a preferred embodiment of the present invention the method includes inflating at least one of the cells with pulses of pressure, the pressure fluctuating between a maximum value and a minimum value during the given time period.

Still further in accordance with a preferred embodiment of the present invention the method includes inflating at least one of the cells to dwell at at least one of a maximum value of pressure and a minimum value of pressure during the given time period.

In accordance with a preferred embodiment of the present invention, wherein for each neighboring pair of cells including a more distal cell and a more proximal cell, the more distal cell is inflated to a tourniquet pressure at the end of the given time period, then the more proximal cell is inflated to the tourniquet pressure, the more distal cell being deflated once the more proximal cell has reached the tourniquet pressure.

There is also provided in accordance with a preferred embodiment of the present invention a method for making a volumetric measurement of a portion of a body, including attaching an inflatable cell about a portion of a body having a first volume, inflating the cell to a predetermined pressure, repeating the two previous steps for a portion of a body having a second volume, and measuring a volumetric change in the inflatable cell, the change being the difference between the first and the second volumes.

In accordance with a preferred embodiment of the present invention the method includes attaching a plurality of the cells along the portion of the body and monitoring the volumetric change in the plurality of cells to obtain a mapping of the placed along the portion of the body.

The methods of the present invention are equally applicable to humans and animals.

BRIEF DESCRIPTION OF THE DRAWINGS

The present invention will be understood and appreciated more fully from the following detailed description, taken in conjunction with the drawings in which:

FIGS. 1A–1D are simplified graphical illustrations of pressure wave forms used in the prior art;

DETAILED DESCRIPTION OF A PREFERRED EMBODIMENT

Figure 2:
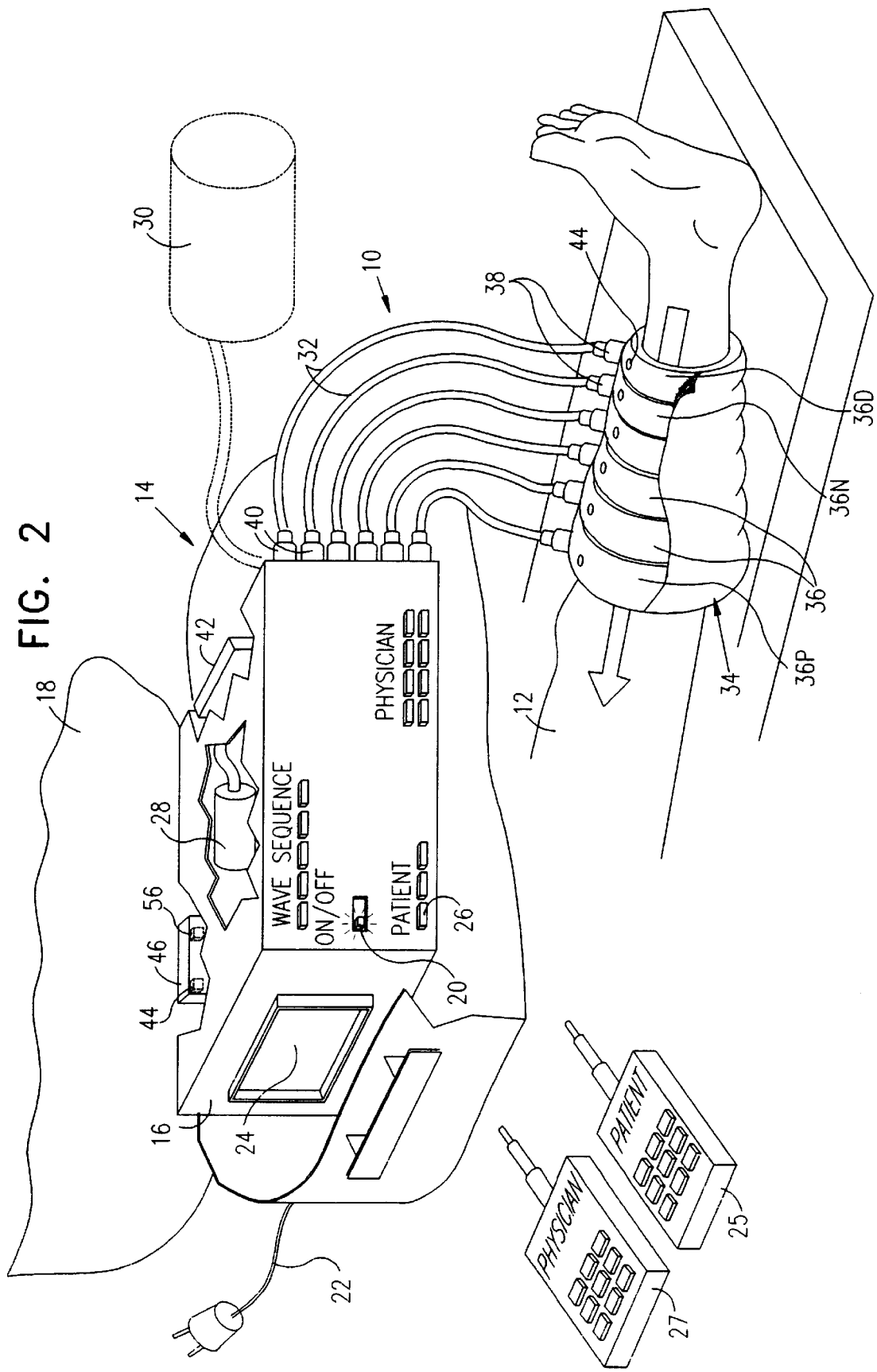
FIG. 2 is a simplified pictorial illustration of apparatus for applying pressure to a portion of a patient, constructed and operative in accordance with a preferred embodiment of the present invention.

Reference is now made to FIG. 2 which illustrates apparatus 10 for applying pressure to a portion of a patient, such as a limb 12, constructed and operative in accordance with a preferred embodiment of the present invention. Apparatus 10 includes a pressure controller 14 which preferably includes a housing 16 constructed of a light weight material, such as molded plastic. A soft-sided travel case 18 may be provided for carrying housing 16. Housing 16 preferably includes a lighted on/off switch 20 and a mains electrical connector 22 for 220 V/50 Hz or 110 V/60 Hz. Alternatively, apparatus 10 may be battery operated. A display 24 is provided for visual annunciation of inflation parameters, such as maximum, minimum and tourniquet pressures, and operational parameters, such as the duration of each time cycle, choice of wave form, alarm and fault conditions. Push buttons 26, or any other interface device such as a keyboard, may be used to input parameters and data. Optionally, remote control units 25 and 27 may be provided for remote operation of apparatus 10 by a patient or physician, respectively. Remote control units 25 and 27 may be in wired or wireless communication with apparatus 10.

Apparatus 10 may include an internal source of pressure 28 such as a compressor. Alternatively, an external source of pressure 30 may be used. Pressure source 28 or 30 supplies pressurized fluid, preferably pressurized air, via a plurality of hoses 32 to a pressure cuff 34 engaged around limb 12. Hoses 32 are preferably connected to pressure source 28 or 30 with quick connect/disconnect connectors which are readily available from a variety of manufacturers. Pressure cuff 34 includes a plurality of individually inflatable cells 36, and each hose 32 is dedicated to one cell 36. Hoses 32 may be connected to cells 36 by suitable connectors 38. Hoses 32 may be conveniently stored in housing 16 when not in use.

At some point in the pressurized fluid connection from source 28 or 30 via hoses 32 to cells 36, there are preferably provided valves 40 for regulating the flow of pressurized fluid to cells 36. For example, valves 40 may be located in housing 16 or on an outer surface thereof. Alternatively, valves 40 may comprise the connection to cuffs 36 instead of connectors 38. Valves 40 are preferably electrically or electronically operated by a valve controller 42 which may be located in housing 16.

Pressure cuff 34 may be constructed as one unit with multiple cells 36, or alternatively, may comprise individual cells 36 aligned one after the other. Cells 36 are placed around limb 12 by any suitable means, such as by VEL-CRO® straps, for example. Cells 36 are arranged so that there is a most distal cell, designated by reference numeral 36D, and a most proximal cell, designated by reference numeral 36P. Pressure sensors or transducers 44 are provided for sensing and monitoring the inflated or deflated pressure in each cell 36. Pressure sensors 44 may be installed in the cells 36 or alternatively may be located remotely from the cells 36. Optionally one pressure sensor 44 may sense pressure in more than one cell. Pressure sensors 44 communicate with a CPU 46, such as a microprocessor, provided in housing 16, which controls inflation of cells 36 as will be described with reference to FIGS. 3, 4A and 4B. Pressure sensors 44 may be optionally located at CPU 46.

Figure 3:
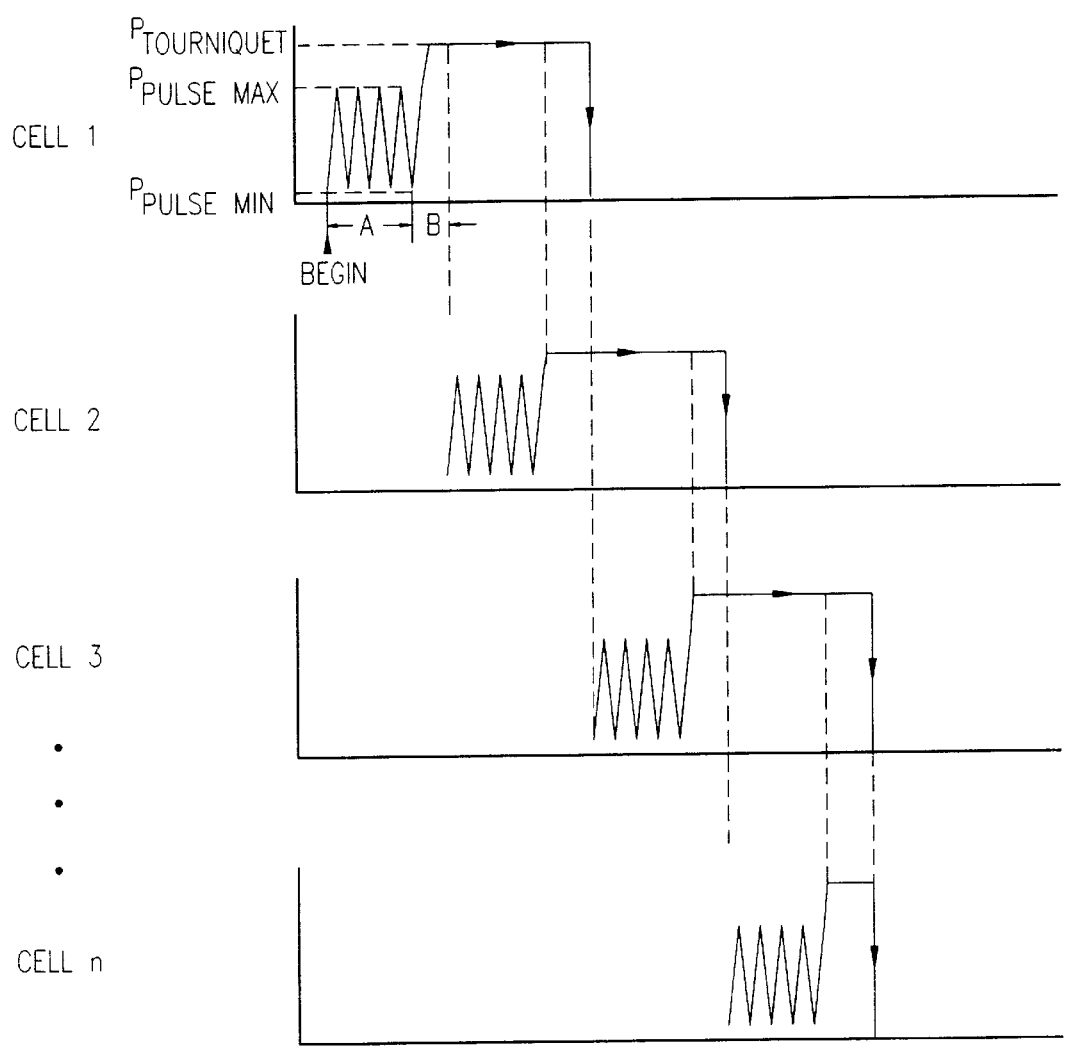
FIG. 3 is a simplified graphical illustration of a peristaltic pulse wave form used in the apparatus of FIG. 2, in accordance with a preferred embodiment of the present invention.
Figure 4A:
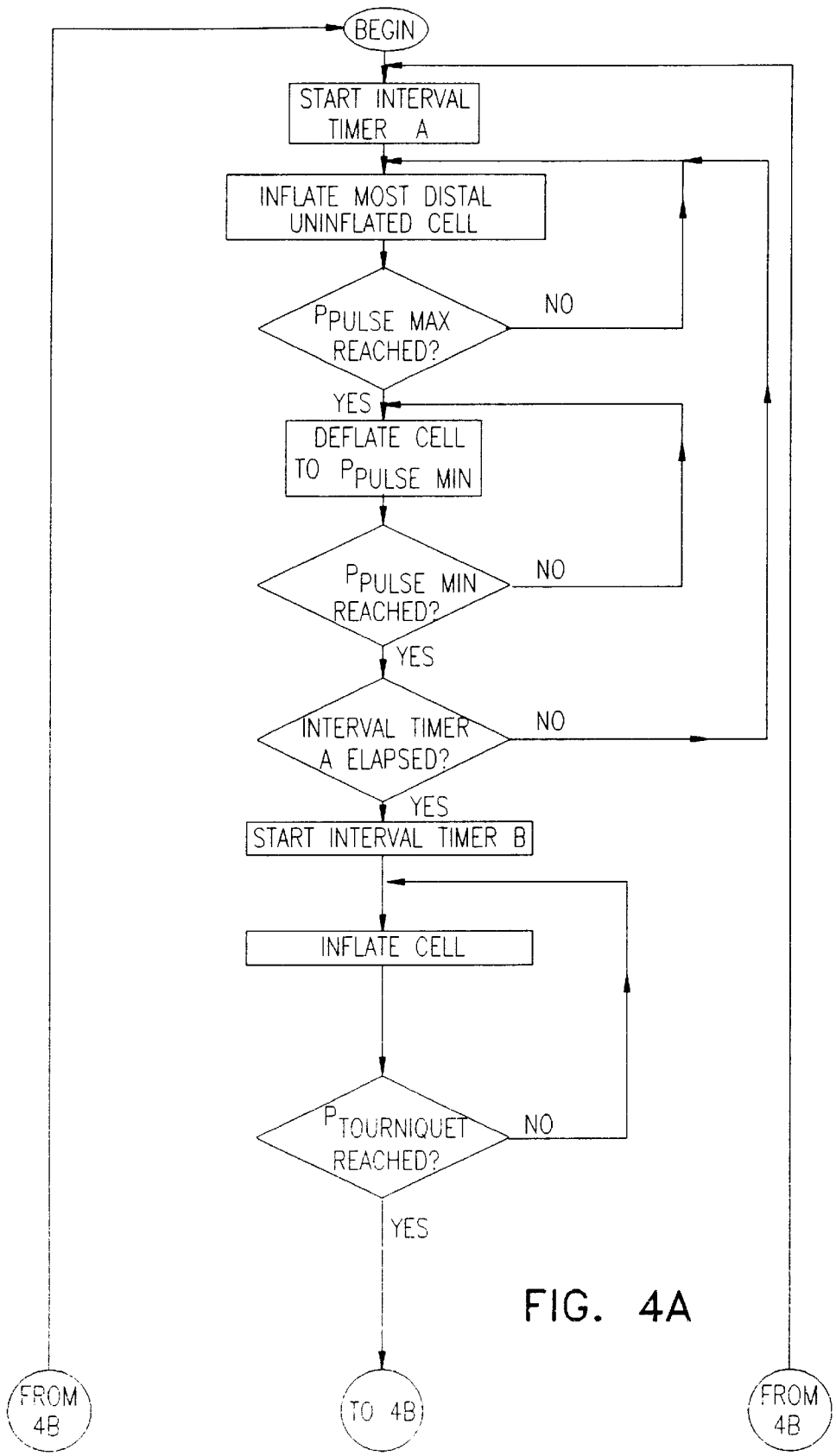
FIGS. 4A and 4B together are a simplified flow chart of the peristaltic pulse wave form used in the apparatus of FIG. 2 in accordance with a preferred embodiment of the present invention.
Figure 4B:
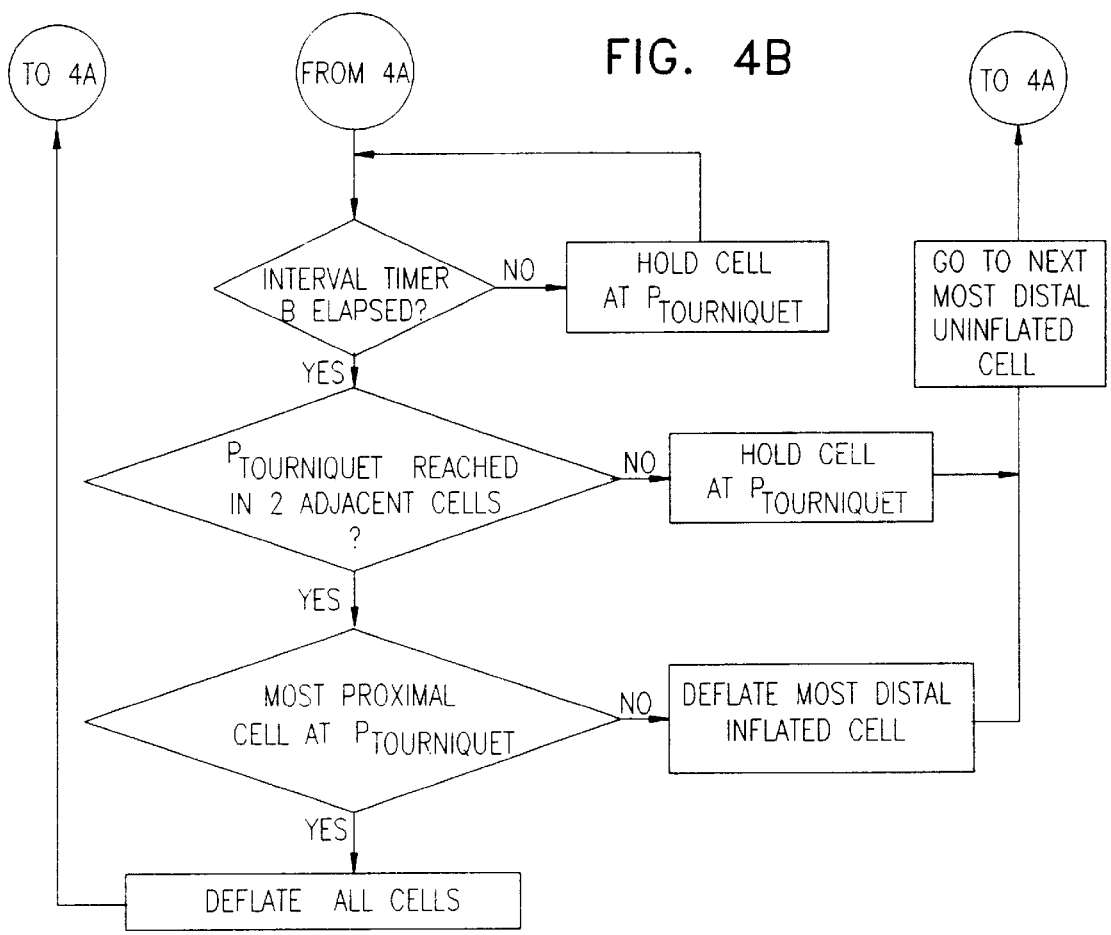

Reference is now made to FIGS. 3 and 4A–4B which respectively are a simplified graphical illustration and a flow chart of a peristaltic pulse wave form used in apparatus 10, in accordance with a preferred embodiment of the present invention. All aspects of the wave form are controlled by CPU 46 of pressure controller 14.

Firstly, a time period for inflation of each cell is selected. It should be understood that each cell may be inflated for the same time period, or alternatively, a different time period may be selected for different cells, depending on the type of treatment required. The most distal cell (cell 36D in FIG. 2) is inflated over the given time period. Cell 36D is not inflated to a constant pressure during the time period, but rather is most preferably inflated with pulses of pressure, the pressure fluctuating between a maximum value, called $P_{pulse\ max}$, and a minimum value, called $P_{pulse\ min}$, during a portion of the given time period, called time interval A. For example, $P_{pulse\ max}$ and $P_{pulse\ min}$ may be in the range of 0–250 mm Hg. The easing of pressure to $P_{pulse\ min}$ allows the engorged tissue to which cell 36D applies pressure, to immediately refill between pressure rises to $P_{pulse\ max}$. The cell thus dynamically decongests the engorged tissue to which the cell applies pressure. The dwell time at each $P_{pulse\ max}$ and $P_{pulse\ min}$ may be selected or preprogrammed as desired, ranging from substantially instantaneous to a few milliseconds or seconds, for example.

Alternatively, other non-constant functions of pressure may be used to inflate cell 36D, such as sinusoidally fluctuating the pressure between $P_{pulse\ max}$ and $P_{pulse\ min}$.

Once time interval A has ended, cell 36D is then inflated to a tourniquet pressure for the remainder of the given time period, called time interval B. The tourniquet pressure may or may not be higher than $P_{pulse\ max}$. While cell 36D is still at tourniquet pressure, the next neighboring cell proximal to cell 36D, designated by reference numeral 36N in FIG. 2, is inflated with pulses of pressure that fluctuate between $P_{pulse\ max}$ and $P_{pulse\ min}$, during a portion of a given time period. In FIG. 3, this portion is equal to time interval A, but it is appreciated that it could be any other time period as well, depending on the required treatment. Once time interval A has ended, cell 36N is inflated to tourniquet pressure for the remainder of the given time period, called time interval B. Again, it is appreciated that the remainder of the time period may alternatively be some other time period other than time interval B.

During time interval B, both neighboring cells 36D and 36N are inflated at tourniquet pressure. At the end of time interval B, cell 36D is deflated. It should be noted that cell 36D does not necessarily have to be deflated to 0 mm Hg, but rather may be deflated to a non-zero gauge pressure. This procedure ensures proximally directed flow of the engorged fluids in the limb and prevents backflow.

The procedure is continued for each neighboring pair of cells until the most proximal cell (36P in FIG. 2) has been inflated and deflated, thus completing one treatment cycle. The treatment cycle may then be repeated as required. Pressure controller 14 may inflate cells 36 in accordance with a programmable inflation scheme, and even in accordance with other wave forms or a combination thereof.

Figure 5A:
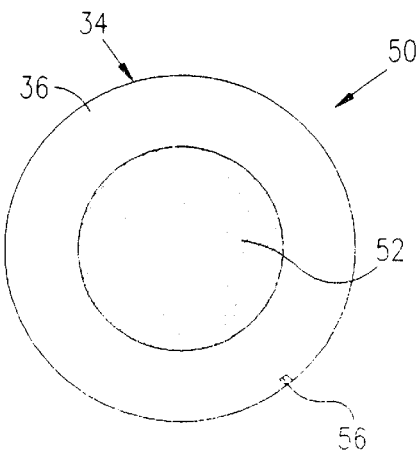
FIGS. 5A and 5B are simplified pictorial illustrations of apparatus for volumetric measurement of a limb of a body, constructed and operative in accordance with a preferred embodiment of the present invention, respectively before and after inflation of a pressure cuff.
Figure 5B:
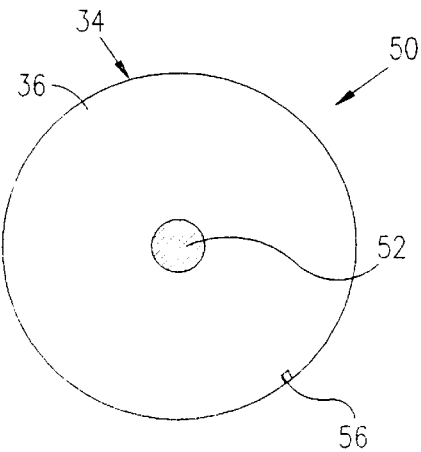

Reference is now made to FIGS. 5A and 5B which illustrate apparatus 50 for volumetric measurement of a limb of a body, constructed and operative in accordance with a preferred embodiment of the present invention. Apparatus 50 is preferably none other than apparatus 10 described hereinabove, wherein cells 36 are placed around a limb 52.

Measuring girth of a limb with a pressure device is known. Cone et al. measures the girth of a limb by measuring the time it takes to inflate the cell until the cell touches the limb periphery and correlating the measured time with the radius (or diameter) of the inflated cell. The present invention uses cell 36 to make a volumetric measurement of the limb with a novel method and apparatus. Instead of measuring time of inflation, a volumetric sensor 56 is provided to measure the volumetric change of cell 36 as it is inflated. For example, in FIG. 5A, cell 36 is placed around limb 52 having a relatively large girth, and cell 36 is pressurized to a certain pressure, e.g., 50 mm Hg. In contrast, in FIG. 5B, limb 52 has a relatively small girth. Again cell 36 is placed around the limb and pressurized to the same pressure as in FIG. 5A. By way of example, FIGS. 5A and 5B may be illustrative of a limb respectively before and after treatment, in which case it is desirable to measure the change in volume at the same location on the limb. As another example, FIGS. 5A and 5B may be illustrative of an edematous limb and a normal limb, respectively, in which case it is desirable to measure the difference in volume of two different limbs.

It is readily noted by comparing FIGS. 5A and 5B, that cell 36 has a larger volume for a smaller girth limb and cell 36 has a smaller volume for a larger girth limb. Volumetric sensor 56 measures the difference in volume of cell 36. The difference in volume of cell 36, kept at constant pressure and temperature, directly provides the difference in volume between the large girth limb of FIG. 5A and the small girth limb of FIG. 5B.

Volumetric sensor 56 may be disposed in each cell 36 or may be disposed in pressure source 28 or 30 (FIG. 2). Volume sensor 56 is preferably in communication with CPU 46 (FIG. 2) such that the volumetric change of each cell 36 may be monitored incrementally, intermittently or continually as desired. CPU 46 may then provide a mapping of limb 52 for each cell 36.

The volumetric measurement of the present invention provides a direct measurement of the limb and is thus more accurate than the prior art.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Apparatus for applying pressure to a portion of a body, comprising:
   a pressure cuff comprising a plurality of individually inflatable cells, comprising a most distal cell and a most proximal cell; and
   a pressure controller that inflates a pair of neighboring cells, one called a distal cell and the other called a proximal cell, in a first mode, second mode, third mode and fourth mode of inflation;
   said first mode of inflation comprising said pressure controller inflating the distal cell with pulses of pressure that fluctuate between a maximum pressure and a minimum pressure during a first time period;
   said second mode of inflation comprising said pressure controller inflating the distal cell to a pressure exceeding said maximum pressure for the remainder of the first time period;
   said third mode of inflation comprising said pressure controller inflating the proximal cell with pulses of pressure that fluctuate between the maximum pressure and the minimum pressure during a second time period, not necessarily equal to the first time period; and
   said fourth mode of inflation comprising said pressure controller at least partially deflating the distal cell at the end of the second time period while maintaining the proximal cell at said pressure exceeding said maximum pressure.

2. Apparatus according to claim 1 and wherein said pressure controller sequentially inflates all to the cells starting with the most distal cell and ending with the most proximal cell in accordance with the first, second, third and fourth modes of inflation, consecutively.

3. Apparatus according to claim 1 wherein said pressure controller inflates at least one of said cells to dwell at at least one of said minimum value of pressure and a said minimum value of pressure during at least one of said first and said second time periods.

4. Apparatus according to claim 1 and wherein said pressure controller comprises a source of pressure and a plurality of valves, each said valve being dedicated to a particular one of said cells, and each said valve being in fluid communication with both said source of pressure and said particular cell.

5. Apparatus according to claim 1 and wherein each said cell comprises a pressure sensor for sensing a pressure of inflation and deflation of said cell.

6. Apparatus according to claim 1 and wherein said pressure controller inflates said cells in accordance with a programmable inflation scheme.

7. Apparatus according to claim 1 and comprising a volumetric sensor that measures a volumetric change in said inflatable cells.

8. A method for applying pressure to a portion of a body, comprising:
   (a) attaching a pressure cuff around an engorged tissue, the cuff comprising a plurality of individually inflatable cells, comprising a most distal cell and a most proximal cell;
   and for a first time period, starting with the most distal cell;
   (b) inflating the cell to a pressure, said pressure fluctuating between a maximum value and a minimum value during said first time period and said pressure comprising a plurality of pressure rises to the maximum pressure;
   (c) allowing the engorged tissue to immediately refill between the pressure rises to the maximum pressure so as to dynamically decongest the engorged tissue;
   (d) inflating the cell to a tourniquet pressure for the remainder of the first time period;
   (e) repeating steps (b) and (d) for the next proximal cell for a second time period, not necessarily equal to the first time period, wherein the cell inflated immediately prior to the adjacent distal cell is at least partially deflated from the tourniquet pressure at the end of the second time period, the next proximal cell remaining at tourniquet pressure; and
   (f) repeating step (e) for each neighboring pair of cells until the most proximal cell has been inflated and deflated.

9. A method according to claim 8 and comprising inflating at least one of said cells to dwell at at least one of said minimum value of pressure and said minimum value of pressure during at least one of said first and said second time periods.

10. A method according to claim 8 wherein the cell inflated immediately prior to the adjacent distal cell is at least partially deflated from the tourniquet pressure to a non-zero pressure.

* * * * *